United States Patent [19]

Kisida et al.

[11] Patent Number: 4,608,389
[45] Date of Patent: Aug. 26, 1986

[54] CARBAMATE COMPOUNDS AND THEIR USE AS INSECTICIDES

[75] Inventors: Hirosi Kisida, Takarazuka; Makoto Hatakoshi, Mino; Sumio Nishida, Takarazuka, all of Japan

[73] Assignee: Sumitomo Chemical Company, Limited, Osaka, Japan

[21] Appl. No.: 639,500

[22] Filed: Aug. 10, 1984

[30] Foreign Application Priority Data

Sep. 7, 1983 [JP] Japan .................. 58-165751

[51] Int. Cl.$^4$ .................. C07C 125/065; A01N 47/12
[52] U.S. Cl. ...................... 514/539; 560/27; 260/455 A; 558/239
[58] Field of Search .................. 560/27; 514/539

[56] References Cited

U.S. PATENT DOCUMENTS 4,215,139  7/1980  Fischer et al. .................. 560/27 X
4,413,010  11/1983  Zurfluh .................. 560/27 X Primary Examiner—Bernard Helfin
Attorney, Agent, or Firm—Birch, Stewart, Kolasch & Birch

[57] ABSTRACT

A compound of the formula:

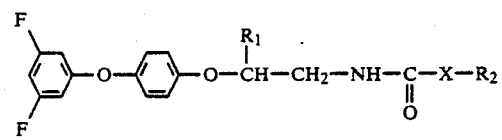

wherein $R_1$ is a hydrogen atom or a methyl group, $R_2$ is a lower alkyl group and X is an oxygen atom or a sulfur atom, which is useful as an insecticide.

15 Claims, No Drawings

CARBAMATE COMPOUNDS AND THEIR USE AS INSECTICIDES

The present invention relates to carbamate compounds, and their production and use. More particularly, it relates to carbamate compounds of the formula:

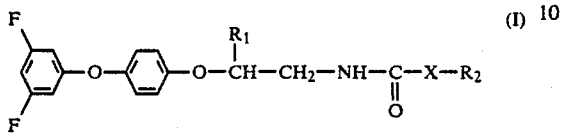

wherein $R_1$ is a hydrogen atom or a methyl group, $R_2$ is a lower alkyl group and X is an oxygen atom or a sulfur atom, and their production and insecticidal use.

Some carbamate compounds are known to exhibit an insecticidal activitiy against larvae of yellow fever mosquito (*Aedes aegypti*), housefly (*Musca domestica*), etc. (U.S. Pat. Nos. 4,215,139 and 4,413,010).

It has been found that the carbamate compounds (I) exhibit a remarkable preventive and controlling effect against harmful insects including larvae of common gnat (*Culex pipiens pallens*), malaria mosquito (Anopheles sp.), etc. in comparison with known carbamate compounds. The present invention is based on the above finding.

The carbamate compounds (I) can be produced by various procedures, of which typical examples are shown below.

Procedure A

A compound of the formula:

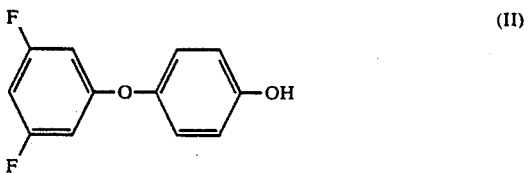

is reacted with a compound of the formula:

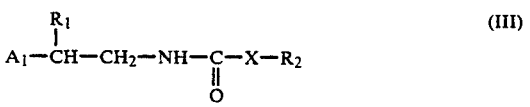

wherein $R_1$, $R_2$ and X are each as defined above and $A_1$ is a leaving group such as a halogen atom (e.g. chlorine, bromine, iodine) or a sulfonyloxy group (e.g. tosyloxy, mesyloxy) in the presence of an acid accepting agent to give the compound (I).

As the acid accepting agent, there may be used an alkali metal (e.g. lithium, sodium, potassium), an alkali metal hydride (e.g. sodium hydride, potassium hydride), an alkali metal amide (e.g. sodium amide, potassium amide), an alkali metal hydroxide (e.g. sodium hydroxide, potassium hydroxide), an alkali metal carbonate (e.g. sodium carbonate, potassium carbonate) or an amine (e.g. triethylamine, trimethylamine, pyridine), etc. The acid accepting agent may be introduced into the reaction system with the other reagent(s). When using the acid accepting agent comprising an alkali metal such as an alkali metal, an alkali metal hydride or an alkali metal amide, it may be first reacted with the compound (II) to give a compound of the formula:

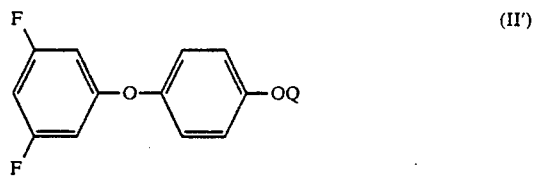

wherein Q is an alkali metal atom, which is then reacted with the compound (III).

The reaction is conveniently carried out in the presence of an inert solvent, of which examples are dimethylformamide, dimethylsulfoxide, dimethoxyethane, hexamethylphosphoric triamide, etc. Although there is no particular limitation to the reaction temperature, it may be generally from $-20°$ to $100°$ C., preferably from $80°$ to $100°$ C. The reaction is normally accomplished within a period of 1 to 50 hours. The molar ratio of the compound (II) or the compound (II') and the compound (III) may be usually 1:0.5–5, preferably 1:1–1.2.

Procedure B

A compound of the formula:

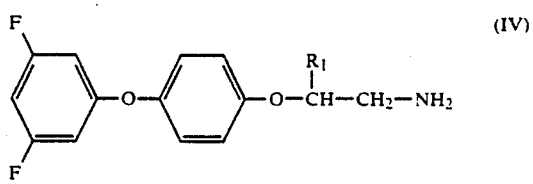

wherein $R_1$ is as defined above is reacted with a compound of the formula:

wherein $R_2$ and X are each as defined above in the presence of an acid accepting agent in an inert solvent to give the carbamate (I).

As the acid accepting agent, there may be used any organic or inorganic base, of which specific examples are an alkali metal carbonate (e.g. sodium carbonate, potassium carbonate), an alkali metal hydroxide (e.g. sodium hydroxide, potassium hydroxide), an aliphatic amine (e.g. trimethylamine, triethylamine), an aromatic base (e.g. pyridine, picoline), etc. Examples of the inert solvent are tetrahydrofuran, diethyl ether, benzene, toluene, methylene chloride, chloroform, carbon tetrachloride, dimethoxyethane, water, etc. These solvents are usable alone or in combination. There is no particular limitation to the reaction temperature, and it is normally from $-30°$ C. to the boiling point of the reaction mixture. The reaction may be in general accomplished within a period of 0.5 to 50 hours. The molar ratio of the compound (IV) and the compound (V) may be usually 1:0.5–2, preferably 1:1–1.2.

Procedure C

A compound of the formula:

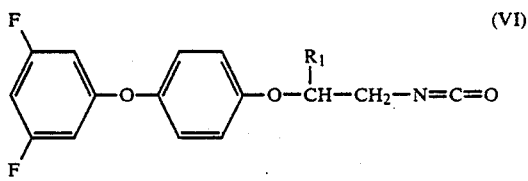

wherein R$_1$ is as defined above is reacted with a compound of the formula:

R$_2$—X—H (VII)

wherein R$_2$ and X are each as defined above in an inert solvent to give the compound (I).

Examples of the inert solvent are dimethylformamide, dimethylsulfoxide, toluene, benzene, etc. These solvents are used alone or in combination. When desired, an organic or inorganic base such as an alkali metal hydride (e.g. sodium hydride), an alkali metal hydroxide (e.g. sodium hydroxide, potassium hydroxide), an aliphatic amine (e.g. triethylamine), an aromatic amine (e.g. pyridine, picoline) may be present in the reaction system so as to accelerate the reaction. No particular limitation is present on the reaction temperature, and it is normally from −20° C. to the boiling point of the reaction mixture. The reaction may be in general accomplished within a period of 1 to 120 hours. The molar ratio of the compound (VI) and the compound (VII) may be usually 1:1–5.

The carbamate compounds (I) of the invention may have the optical isomers, which are also included within the scope of the invention.

The starting compound (II) is novel and may be produced in a procedure similar to the one as described in Angew.Chem., 52, 915 (1938) and Japan Kokai No. 55-62033. The compounds (IV) and (VI) are also novel and can be produced from the compound (II) in accordance with the method as described in U.S. Pat. No. 4,215,139. Productions of these compounds are schematically shown below:

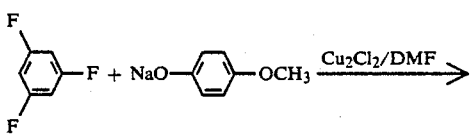

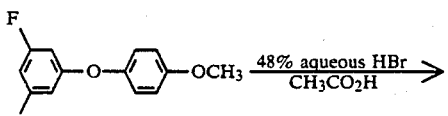

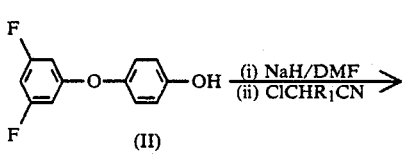

(II)

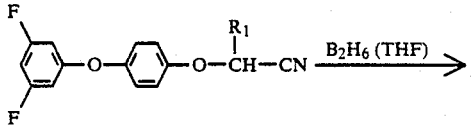

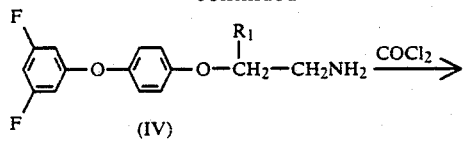

(IV)

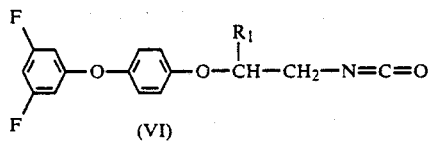

(VI)

wherein R$_1$ is as defined above.

The compounds (III) and (V) are known.

A typical embodiment for production of the carbamate compound (I) is shown in the following Example.

EXAMPLE 1

A mixture of 4-(3,5-difluorophenoxy)phenol (0.50 g), ethyl N-2-chloroethylcarbamate (0.375 g), potassium carbonate (0.621 g) and anhydrous dimethylformamide (10 ml) was stirred at 100° C. for 3 hours, followed by cooling to room temperature. Ice-water (50 ml) was poured to the resultant mixture, which was extracted with toluene (50 ml). The toluene extract was washed with water and dried over anhydrous sodium sulfate. The toluene extract was concentrated under reduced pressure to give an oily residue. The residue was purified by silica gel column chromatography to give 0.605 g of ethyl N-2-[4-(3,5-difluorophenoxy)phenoxy]ethylcarbamate as a colorless liquid. n$_D^{25.5}$ 1.5305.

In the similar manner as above, there were produced the carbamate compounds (I), of which some examples are shown in Table 1.

TABLE 1

 (I)

| Compound No. | R$_1$ | R$_2$ | X | Physical constant |
|---|---|---|---|---|
| 1 | H | CH$_3$ | O | n$_D^{25.0}$ 1.5362 |
| 2 | H | C$_2$H$_5$ | O | n$_D^{25.5}$ 1.5305 |
| 3 | H | i-C$_3$H$_7$ | O | n$_D^{25.0}$ 1.5276 |
| 4 | CH$_3$ | C$_2$H$_5$ | O | n$_D^{27.0}$ 1.5224 |
| 5 | H | C$_2$H$_5$ | S | n$_D^{26.5}$ 1.5597 |

On the application of the carbamate compound (I) as an insecticidal agent, it may be formulated in a conventional composition form such as an emulsifiable concentrate, a dust, a granule, a wettable powder or a fine granule. The content of the carbamate compound (I) in such composition is usually from about 0.1 to 99.9% by weight, preferably from about 2 to 80% by weight.

Formulation may be achieved by a per se conventional manner by mixing at least one of the carbamate compounds (I) with an appropriate solid or liquid carrier(s) or diluent(s). An appropriate adjuvant(s) such as a surfactant, an adherent, a dispersant and a stabilizers may be incorporated therein for improving the dispersibility and/or other properties of the active ingredient.

Examples of the solid carrier or diluent are clay (e.g. kaolin, bentonite, fuller's earth, pyrophyllite, sericite), talc, inorganic materials (e.g. hydrated silica, pumice, diatomaceous earth, sulfur powder, active carbon), etc. in fine powders or powdery form.

Examples of the liquid carrier or diluent are alcohols (e.g. methanol, ethanol), ketones (e.g. acetone, methyl ethyl ketone), ethers (e.g. diethyl ether, dioxane, cellosolve, tetrahydrofuran), aromatic hydrocarbons (e.g. benzene, toluene, xylene, methylnaphthalene), aliphatic hydrocarbons (e.g. gasoline, kerosene, lamp oil), esters, nitriles, acid amides (e.g. dimethylformamide, dimethylacetamide), halogenated hydrocarbons (e.g. dichloroethane, trichloroethylene, carbon tetrachloride), etc.

Examples of the surfactant are alkylsulfates, alkylsulfonates, alkylarylsulfonates, polyethylene glycol ethers, polyhydric alcohol esters, etc. Examples of the adherent and dispersant may include casein, gelatin, starch powder, CMC (carboxymethyl cellulose), gum arabic, alginic acid, ligninsulfonate, bentonite, molasses, polyvinyl alcohol, pine oil and agar. As the stabilizers, there may be used PAP (isopropyl acid phosphates mixture), TCP (tricresyl phosphate), tolu oil, epoxydized oil, various surfactants, various fatty acids and their esters, etc.

Some practical embodiments of the composition for the control of insects according to the invention are illustratively shown in the following Formulation Examples wherein % and part(s) are by weight.

FORMULATION EXAMPLE 1

Each of Compound Nos. 1 to 5 (20 parts), an emulsifier (a mixture of polyoxyethylene-styrenated phenyl ether, polyoxyethylene-styrenated phenyl ether polymer and an alkylarylsulfonate) (20 parts) and xylene (60 parts) are mixed well to make an emulsifiable concentrate.

FORMULATION EXAMPLE 2

Each of Compound Nos. 1 to 5 (20 parts) and an emulsifier (sodium laurylsulfate) (5 parts) are mixed well, and diatomaceous earth (300 mesh) (75 parts) is added thereto, and the resultant mixture is mixed well in a pulverizer to make a wettable powder.

FORMULATION EXAMPLE 3

Each of Compound Nos. 1 to 5 (3 parts) is dissolved in acetone (20 parts), talc (300 mesh) (97 parts) is added thereto, and the resultant mixture is mixed well in a pulverizer. Then, acetone is eliminated by evaporation to give a dust.

FORMULATION EXAMPLE 4

Each of Compound Nos. 1 to 5 (5 parts), a dispersant (calcium ligninsulfonate) (2 parts) and clay (93 parts) are mixed well in a pulverizer. To the resultant mixture, water is added in an amount of 10%, and the resulting mixture is kneaded well and granulated by the aid of a granulator, followed by drying to give a granule.

The following Examples are some typical test results showing the excellent insect control activity of the carbamate compound (I).

TEST EXAMPLE 1

An emulsifiable concentrate formulated according to Formulation Example 1 was diluted with water to make a designed concentration. The dilution (0.5 ml) was added to 100 ml of distilled water. Twenty last instar larvae of common mosquito (*Culex pipiens pallens*) were released therein and reared until their emergence. The 50% emergence inhibition concentration ($IC_{50}$) (ppm) was determined (two replications), from which the activity ratio was calculated according to the following equation:

$$\text{Activity ratio} = \frac{IC_{50} \text{ of Comparison compounds}}{IC_{50} \text{ of Invention compounds}}$$

The Comparison compounds are the non-fluorinated derivatives corresponding to the Invention compounds and described in U.S. Pat. No. 4,215,139. For instance, the Comparison compound corresponding to the Invention compound (2) is ethyl N-2-(4-phenoxyphenoxy)ethylcarbamate.

The results are shown in Table 2.

TABLE 2

| Test Compound No. | Activity ratio |
| --- | --- |
| 1 | 80 |
| 2 | 120 |
| 3 | 80 |
| 4 | 90 |
| 5 | 100 |

TEST EXAMPLE 2

Powdered animal feed (2 g) was thoroughly mixed with bran (14 g). An emulsifiable concentrate formulated according to Formulation Example 1 was diluted with water to make a designed concentration and the dilution (28 ml) was added to the above mixture. The resultant mixture was stirred well to make an artificial culture. Thirty 4-day-old larvae of housefly (*Musca domestica*) were reared therein until their pupation. The obtained pupae were placed into a plastic cup, and the rate of emergence was determined. According to the following equation, the emergence inhibition (%) was calculated:

Emergence inhibition (%) =

$$\left(1 - \frac{\text{Rate of emergence in treated plot}}{\text{Rate of emergence in untreated plot}}\right) \times 100$$

The results are shown in Table 3.

TABLE 3

| Test compound No. | Emergence inhibition (%) | | |
| --- | --- | --- | --- |
| | 3 ppm | 1 ppm | 0.3 ppm |
| 2 | 89 | 65 | 32 |
| Comparison compound A[1] | 4 | 0 | 0 |
| Comparison Compound B[2] | 22 | 7 | 7 |

Note:
[1] Ethyl N—2-(4-phenoxyphenoxy)ethylcarbamate as covered in U.S. Pat. No. 4,215,139;
[2] Ethyl N—2-[4-(3-fluorophenoxy)-phenoxy]ethylcarbamate as described in U.S. Pat. No. 4,215,139.

What is claimed is:
1. A compound of the formula:

$$\text{F}_2\text{C}_6\text{H}_3-\text{O}-\text{C}_6\text{H}_4-\text{O}-\underset{\underset{R_1}{|}}{\text{CH}}-\text{CH}_2-\text{NH}-\underset{\underset{O}{\|}}{\text{C}}-\text{X}-R_2$$

wherein $R_1$ is a hydrogen atom or a methyl group, $R_2$ is an ethyl group and X is an oxygen atom.

2. The compound according to claim 1, wherein $R_1$ is a hydrogen atom.

3. The compound according to claim 1, which is represented by the formula:

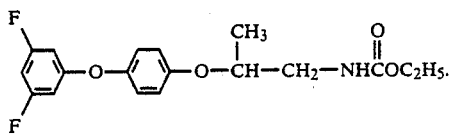

4. An insecticidal composition which comprises as an active ingredient an insecticidally effective amount of the compound according to claim 1, and an appropriate solid or liquid carrier(s) or diluent(s).

5. An insecticidal composition which comprises as an active ingredient an insecticidally effective amount of the compound according to claim 2, and an appropriate solid or liquid carrier(s) or diluent(s).

6. An insecticidal composition which comprises as an active ingredient an insecticidally effective amount of the compound according to claim 3, and an appropriate solid or liquid carrier(s) or diluent(s).

7. A method for controlling harmful insects which comprises applying an insecticidally effective amount of the compound according to claim 1 to the harmful insects.

8. A method for controlling harmful insects which comprises applying an insecticidally effective amount of the compound according to claim 2 to the harmful insects.

9. A method for controlling harmful insects which comprises applying an insecticidally effective amount of the compound according to claim 3 to the harmful insects.

10. The method according to claim 7, wherein the harmful insects are common mosquito (*Culex pipiens pallens*).

11. The method according to claim 7, wherein the harmful insects are houseflies (*Musca domestica*).

12. The method according to claim 8, wherein the harmful insects are common mosquito (*Culex pipiens pallens*).

13. The method according to claim 3, wherein the harmful insects are houseflies (*Musca domestica*).

14. The method according to claim 8, wherein the harmful insects are houseflies (*Musca domestica*).

15. The method according to claim 3, wherein the harmful insects are common mosquito (*Culex pipiens pallens*).

* * * * *